US007312765B2

(12) United States Patent
de Wit et al.

(10) Patent No.: US 7,312,765 B2
(45) Date of Patent: Dec. 25, 2007

(54) DISPLAY SYSTEM AND METHOD FOR REDUCING THE MAGNITUDE OF OR ELIMINATING A VISUAL ARTIFACT CAUSED BY A SHIFT IN A VIEWER'S GAZE

(75) Inventors: Gerard de Wit, Culemborg (NL); John Lewis, Bellevue, WA (US); Bernie Murray, Seattle, WA (US); Clarence Tegreene, Redmond, WA (US)

(73) Assignee: Microvision, Inc., Redmond, WA (US)

( * ) Notice: Subject to any disclaimer, the term of this patent is extended or adjusted under 35 U.S.C. 154(b) by 394 days.

(21) Appl. No.: 10/361,095

(22) Filed: Feb. 6, 2003

(65) Prior Publication Data

US 2004/0155834 A1 Aug. 12, 2004

Related U.S. Application Data

(63) Continuation-in-part of application No. 09/129,739, filed on Aug. 5, 1998, now Pat. No. 6,583,772.

(51) Int. Cl.
*G09G 5/00* (2006.01)
*A61B 3/00* (2006.01)

(52) U.S. Cl. .............................. 345/7; 345/8; 345/611; 345/629; 351/209; 351/221

(58) Field of Classification Search ................ 345/7–9, 345/611, 629; 600/558; 382/100, 103; 359/726; 351/200, 209, 221
See application file for complete search history.

(56) References Cited

U.S. PATENT DOCUMENTS

| | | | | |
|---|---|---|---|---|
| 5,701,132 | A | 12/1997 | Kollin et al. | |
| 6,120,461 | A * | 9/2000 | Smyth | 600/558 |
| 6,157,352 | A | 12/2000 | Kollin et al. | |
| 6,245,590 | B1 | 6/2001 | Wine et al. | |
| 6,315,412 | B1 * | 11/2001 | Snodderly et al. | 351/200 |
| 6,583,772 | B1 * | 6/2003 | Lewis et al. | 345/7 |
| 2002/0181733 | A1 * | 12/2002 | Peck | 382/100 |
| 2004/0075914 | A1 * | 4/2004 | Yamamoto | 359/726 |

FOREIGN PATENT DOCUMENTS

| | | |
|---|---|---|
| WO | WO 01/33282 A1 | 5/2001 |
| WO | WO 01/33298 | 5/2001 |

* cited by examiner

*Primary Examiner*—David L. Lewis
(74) *Attorney, Agent, or Firm*—Graybeal Jackson Haley

(57) ABSTRACT

A display system includes an image generator that generates an image and a control circuit that reduces or eliminates the viewer's perception of a visual artifact when the viewer's gaze shifts with respect to the image. For example, such a display system may generate a fill-in light to reduce or eliminate the viewer's perception of flicker or other visual artifacts when the viewer shifts his gaze with respect to an exit pupil through which the generated image is viewed. The system may match the fill-in light's brightness, color, or both the brightness and color to the brightness and/or color of the image.

45 Claims, 5 Drawing Sheets

DISPLAY SYSTEM AND METHOD FOR REDUCING THE MAGNITUDE OF OR ELIMINATING A VISUAL ARTIFACT CAUSED BY A SHIFT IN A VIEWER'S GAZE

CROSS-REFERENCE TO RELATED APPLICATION

This is a continuation-in-part of Ser. No. 09/129,739 that claims benefit of U.S. Pat. No. 6,583,772, filed on Aug. 5, 1998, and co-pending at the time this application was made.

TECHNICAL FIELD

The invention relates generally to image display/projection systems, and more particularly to a display system, such as a retinal scanning display (RSD) system, and a method for reducing the magnitude of or eliminating a visual artifact that a viewer may otherwise perceive when viewer shifts the direction of his gaze by moving his eye pupil.

BACKGROUND

A display such as a retinal scanning display (RSD) system typically generates images for viewing, and such images are typically graphical or video. A graphical image, i.e., graphic, typically changes infrequently or not at all. For example, a flight-instrument graphic of cockpit instruments may overlay a pilot's view. Typically, there is little change in this graphic other than the movement of the instrument pointers or numbers. Conversely, video images are a series of frames that typically change frequently to show movement of an object or the panning of a scene. For example, a television displays video images.

One aspect of a typical display system is the system's exit pupil, which defines the "window" through which the viewer can perceive an image when the pupil of the viewer's eye is aligned with the exit pupil. In a simplistic analogy, the exit pupil is much like a keyhole in a door. If the viewer's eye pupil is aligned with the keyhole, then the light which defines the image passes through the keyhole and enters the eye through the eye pupil such that the viewer perceives the image. However, if the viewer's eye pupil moves relative to the keyhole such that the light from the keyhole does not enter the eye pupil, then the viewer will not perceive the image. In some applications the display system generates two images, each via a respective exit pupil for each eye. This can allow the viewer to see a composite image stereoscopically.

As the viewer shifts his gaze within his field of view, the physical rotation of the viewer's eye may cause the viewer's eye pupil to move relative to the exit pupil. If the viewer's eye pupil moves sufficiently far, it can move out of alignment with the exit pupil. More specifically, the viewer will perceive an image as long a portion of the eye pupil is aligned with a portion of the exit pupil. That is, the viewer will still perceive the image as long as light from the exit pupil enters the eye pupil (although the viewer's perception of the image may vary depending on the degree of alignment between the eye pupil and the exit pupil). Assuming that the diameter of a human viewer's eye pupil typically ranges from about 2 millimeters (mm) in bright light to about 7 mm in dim light and that the width and height of the exit pupil are always smaller (e.g., 1 mm) than the diameter of the viewer's eye pupil, the viewer can move his eye over a range approximately equal to the sum of the diameter of his eye pupil and the width/height of the exit pupil (e.g., 3-8 mm) without losing sight of the image. But if the viewer shifts his gaze such that his eye pupil moves beyond this range—which he often does—then he typically loses sight of the image. While this example assumes, for simplicity of explanation, that the exit pupil is smaller than the eye pupil, this is not always the case. However, the basic concepts can still apply even where the eye pupil is larger than the exit pupil.

To prevent the viewer from losing sight of an image as he shifts his gaze, an RSD system may include a tracking display system to track the movement of the viewer's eyes and to move the exit pupils to keep them aligned with the respective eye pupils. An example of a tracking RSD is disclosed in commonly assigned International Publication WO 01/33282, filed Oct. 29, 1999, which is incorporated herein by reference.

A common problem with a tracking display system is that it may allow a viewer to perceive visual artifacts when he shifts his gaze. A visual artifact is an undesired phenomenon that a viewer perceives in an image. For example, flicker, which is a rapid fluctuation in brightness, is a visual artifact that a viewer may perceive in an image, particularly a raster-scanned image. Because a viewer's eyes can typically move faster than the display system can track the movement—a viewer's eyes can typically rotate at angular velocities up to 500°/second—there is often a slight delay between the time when the eye pupils attain their new positions and the time when the respective exit pupils become realigned with the eye pupils. During this period of misalignment, the viewer may perceive that a composite image is flickering, particularly if the display system is a raster-scanning type of display. Specifically, during the period of misalignment, light from the composite image does not enter the eye pupils, and thus the image can "disappear" until the display system realigns each exit pupil with its corresponding eye pupil. Thus, the viewer may perceive this momentary "disappearance" and the subsequent "reappearance" of the image as an artifact such as flicker.

Moreover, the viewer's perception of flicker may be exacerbated if the display produces the perceived image with raster-scanned, modulated beams of light. Because the peripheral rods and cones (responsible for peripheral vision) of the human eye have relatively fast response times, they, unlike the straight-ahead rods and cones (responsible for straight-ahead vision), may detect the flicker inherent in a scanned image if the scanning frequency is too low. Consequently, as the eye pupil and the exit pupil come into alignment, light from the exit pupil may initially strike the peripheral rods and cones. Consequently, the increased flicker sensitivity of the peripheral rods and cones may increase the viewer's perception of flicker.

Unfortunately, visual artifacts such as flicker may annoy or distract the viewer. For example, if the display system generates a flight-instrument overlay graphic, such visual artifacts may distract or irritate the pilot or slow the pilot's response time.

An expanded-exit-pupil display system can eliminate the need to track eye movements by generating one or more arrays of multiple identical exit pupils—typically an equal number of arrays for each eye—such that at least one exit pupil is always aligned with each pupil as the viewer shifts his gaze. Each array, often called an expanded exit pupil, is the region within which the individual exit pupils are located. The effective size of the expanded exit pupil is defined by the region of the eye's field of view (FOV) over which the exit pupils are distributed. This is often called the "eye box."

Unlike the single exit pupil of the tracking RSD system discussed above, which has a single exit pupil for each eye, the cross-sectional dimensions of the expanded exit pupil are significantly larger than the diameter of the corresponding eye pupil. And ideally, the gaps between the exit pupils with the expanded exit pupil will be less than the diameter of the viewer's eye pupil. Consequently, as long as the viewer's gaze remains within the ideal expanded exit pupil, he will see the composite image because at least one of the exit pupils within each expanded exit pupil will always be aligned with the respective pupils of the viewer's eyes. Examples of a RSD system that generates an expanded exit pupil are disclosed in U.S. Pat. Nos. 5,701,132 and 6,157,352, which are incorporated by reference.

Unfortunately, generating and maintaining an ideal and sufficiently large and uniform expanded exit pupil may be difficult in many applications. Additionally, a large exit pupil may require more optical energy for a given perceived brightness. Consequently, it may be desirable to combine tracking with an expanded-exit-pupil display. An example of such a combination display system is disclosed in commonly assigned International Publication WO 01/33282, filed Oct. 29, 1999, which is incorporated by reference. Such a system may suffer from the same problems as the tracker and expanded-exit-pupil display systems discussed above.

Consequently, with many expanded exit pupils, the viewer may perceive visual artifacts even when he shifts his gaze such that it remains aligned with the expanded exit pupil. For example, if the gaps between the individual exit pupils within the expanded exit pupil are greater than the diameter of the viewer's eye pupil, then the viewer may perceive flicker as his pupil moves from a starting exit pupil to a destination exit pupil. This flicker is caused by the viewer's eye pupil losing alignment with the starting exit pupil before becoming aligned with the destination exit pupil (i.e., like moving from "keyhole" to "keyhole"). The flicker may be especially noticeable when the intensity or other characteristics of the respective images viewed through the starting and destination exit pupils are different. Furthermore, if the system is a tracking system, then the viewer may perceive additional flicker as the expanded exit pupil follows the movement of the viewer's eyes.

SUMMARY

In one aspect according to the invention, a display system includes an image generator that generates an image and a circuit that reduces or eliminates the viewer's perception of a visual artifact when the viewer's gaze shifts with respect to the image.

For example, such a display system may generate a fill-in light to reduce or eliminate the viewer's perception of flicker or other visual artifacts when the viewer shifts his gaze in a manner that moves his eye pupil with respect to an exit pupil. In addition, the system may match the fill-in light's brightness, color, or both the brightness and color, to the brightness and/or color of the image.

DETAILED DESCRIPTION

Figure 1:
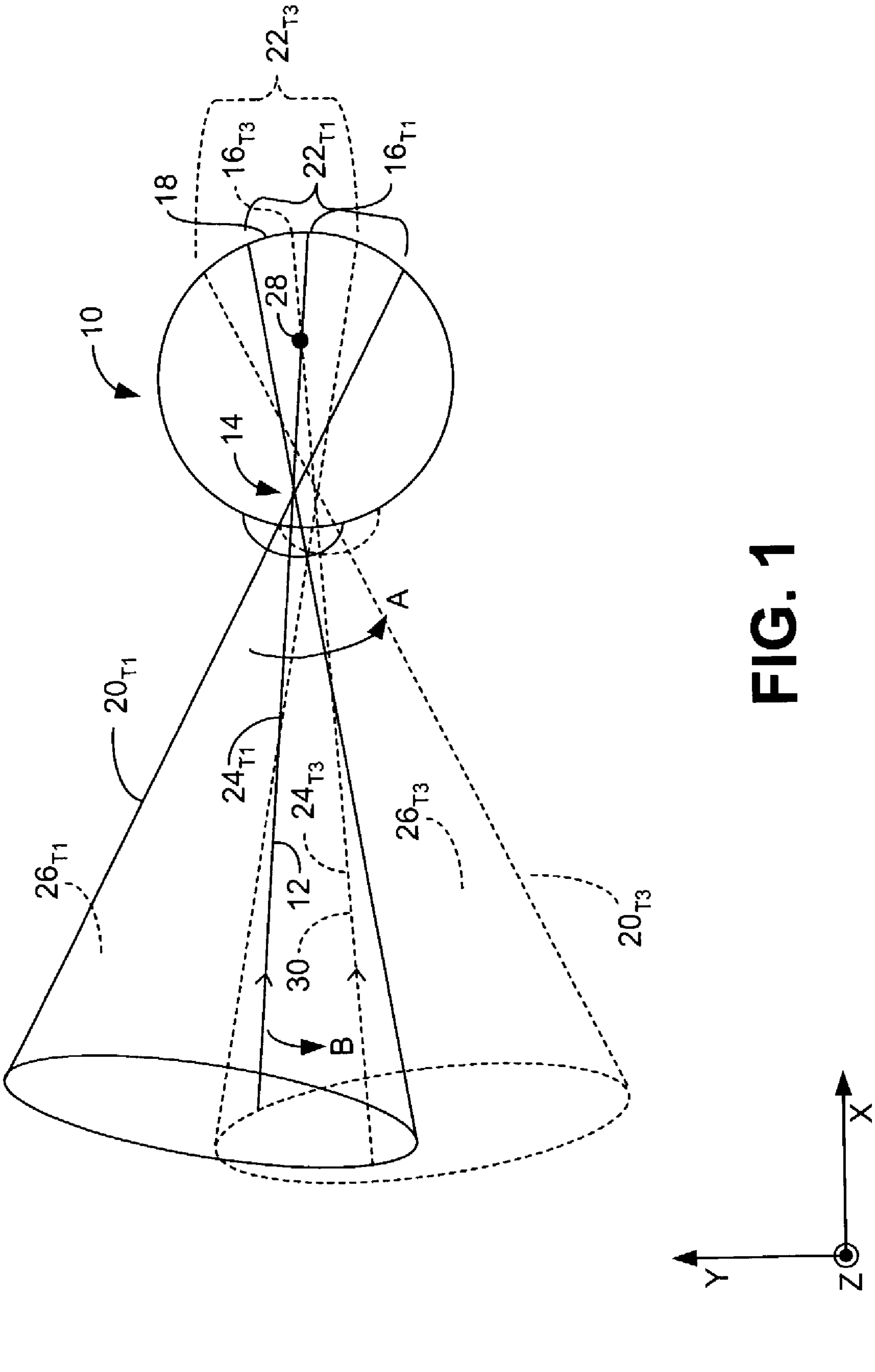
FIG. 1 is a diagram that shows how a display system such as a tracking RSD system can reduce or eliminate visual artifacts such as flicker when a viewer shifts his gaze according to an embodiment of the invention.

FIG. 1 is a diagram that shows how a display system such as a tracking RSD system (FIG. 2) can reduce or eliminate visual artifacts as a viewer shifts his gaze according to an embodiment of the invention. For purposes of explanation, the page that FIG. 1 is drawn on lies in the X-Y plane, and the Z axis is perpendicular to the page. Furthermore, although only one of the viewer's (viewer not shown) eyes is shown and discussed, a similar discussion can apply to the viewer's other eye in a binocular or bi-ocular system, such as a system that generates a composite image for stereoscopic viewing. Therefore, as used in this discussion, "the viewer's field of view" denotes the field of view available to one or both of the viewer's eyes in the monocular or binocular system, as the case may be. The "eye's field of view" or "the pupil's field of view" denotes the field-of-view component available to one of the viewer's eyes.

Figure 2:
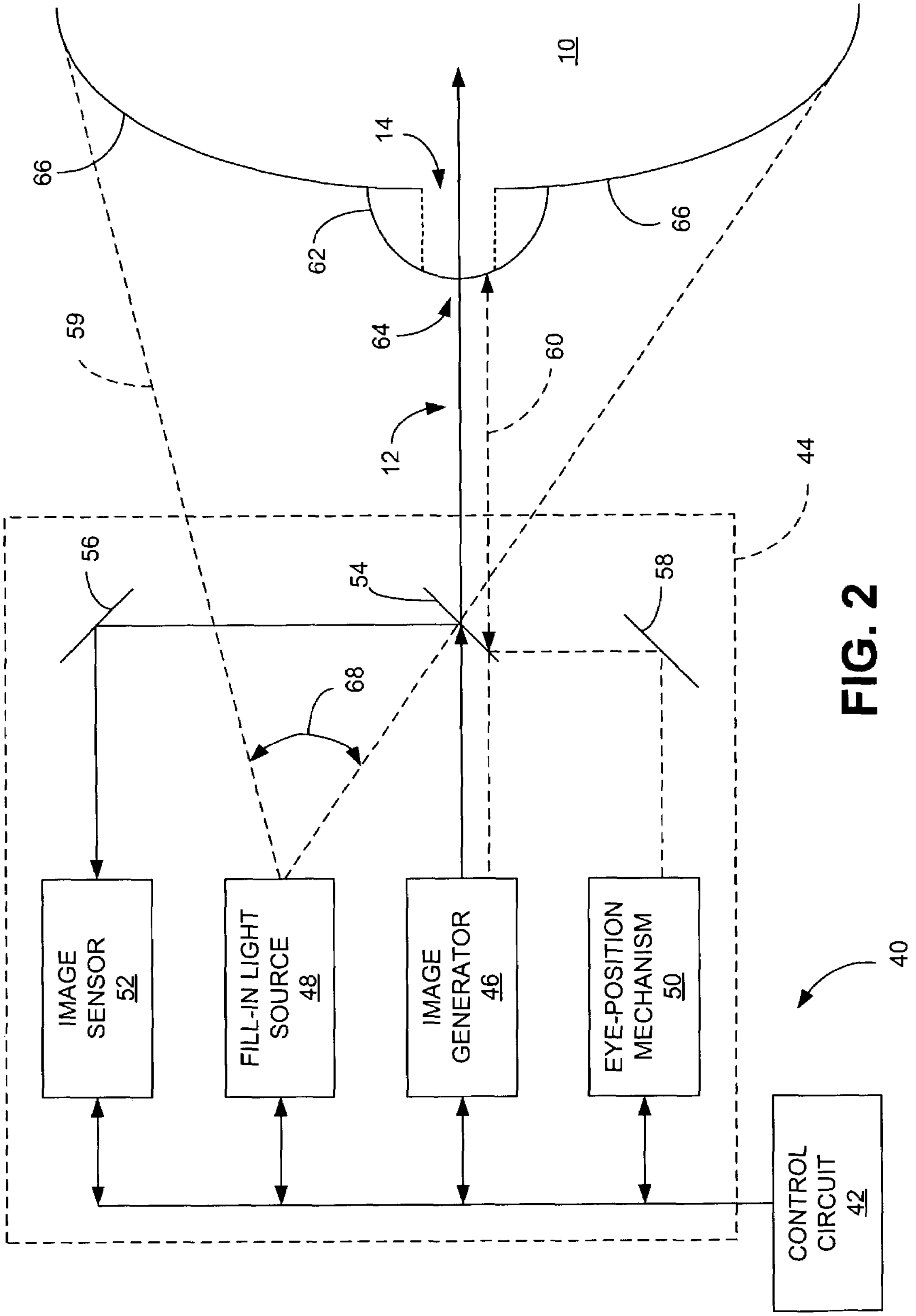
FIG. 2 is a diagram of a tracking RSD system that can operate according to the techniques disclosed in FIG. 1 according to an embodiment of the invention.

At an initial time T1, a viewer's eye 10 is in a steady-state orientation and is aligned with an exit pupil 12, which is generated by a tracking RSD system such as the system of FIG. 2. Thus, the viewer perceives an image via the exit pupil 12. More specifically, the eye's pupil 14 is aligned with the exit pupil 12 such that the eye's lens (not shown) focuses the image onto a center region $\mathbf{16}_{T1}$ (the center region 16 at the time T1) of the eye's retina 18. The eye 10 has a field of view (FOV) $\mathbf{20}_{T1}$, which is the conical viewing region that extends from the pupil 14 and that impinges upon a region $\mathbf{22}_{T1}$ of the retina 18. Because the pupil 14 is aligned with the exit pupil 12, the center axis $\mathbf{24}_{T1}$ of the FOV $\mathbf{20}_{T1}$ is aligned with the exit pupil 12. Consequently, like the exit pupil 12, and the center axis $\mathbf{24}_{T1}$ intersects the center region $\mathbf{16}_{T1}$ of the retina 18. In actuality, the lens of the eye 10 may alter the dimensions of the region $\mathbf{22}_{T1}$, and, although represented by a line, the exit pupil 12 has a finite, nonzero diameter. But FIG. 1 is sufficient for purposes of explanation.

At a time T2, the eye 10 begins rotating (as indicated by the arrow A) about an axis 28, which is parallel to the Z axis, toward a path 30 that has the same dimensions as the exit pupil 12. Of course the pupil 14, and thus the eye's FOV 20, follow the rotation of the eye 10.

At a time T3, the eye 10 stops rotating at another steady-state position where the pupil 14 is aligned with the path 30. Consequently, the center axis $\mathbf{24}_{T3}$ of the FOV $\mathbf{20}_{T3}$ is aligned with the path 30, and the center axis and the path both intersect the center region $\mathbf{16}_{T3}$ of the retina 18.

At time T2 or shortly thereafter, the RSD system (FIG. 2) detects that the eye 10 is rotating away from its T1 position, and attempts to track this rotation by keeping the exit pupil 12 aligned with the FOV center axis 24—the arrow B indicates the direction in which the RSD system moves the exit pupil 12 during this tracking period. But if the eye 10 rotates too fast, then the RSD system can't keep up, and the exit pupil 12 lags behind the center axis 24. Initially, the distance between the exit pupil 12 and center axis 24 increases such that the exit pupil effectively moves from the eye's straight-ahead zone of vision, to its peripheral zone of vision, and altogether out the eye's zone of vision.

At a time T4 after the eye 10 stops rotating—the eye stops rotating at time T3—the exit pupil 12 "catches up" to the center axis $\mathbf{24}_{T3}$, and thus overlaps the path 30. Consequently, the RSD system has effectively moved the exit pupil 12 from outside of the eye's zone of vision back into the eye's straight-ahead zone of vision. Although in this example, the exit pupil 12 effectively moved outside of the eye's FOV 20, the analysis is similar where the exit pupil moves to the eye's peripheral zone of vision.

As discussed in the Background section of this application, the viewer (not shown) may perceive flicker or other visual artifacts during the period between times T2 and T4 when the exit pupil 12 effectively moves from the viewer's straight-ahead zone of vision, through the viewer's peripheral zone of vision, to outside the viewer's zone of vision, and then back to the straight-ahead zone.

Furthermore, the viewer's other eye and the exit pupil through which that eye views the image or composite image (neither the other exit pupil nor the other eye is shown) act the same or approximately the same way as the eye 10 and exit pupil 12 during the period from T1-T4.

Still referring to FIG. 1, in one embodiment, the RSD system (FIG. 2) reduces or eliminates the viewer's (viewer not shown) perception of visual artifacts during the period between times T2 and T4 by briefly illuminating at least a portion of the viewer's composite FOV—the FOV 20 is the portion of the composite FOV attributed to the eye 10. This "fill-in" light makes the lagging exit pupil 12 (perceived as a lagging image by the viewer) less noticeable by temporarily raising the brightness level of the illuminated portion of the viewer's composite FOV. That is, the brighter the illuminated portion of the viewer's FOV, the less likely that the viewer will perceive the lagging exit pupil 12 as flicker or as some other visual artifact. This is the same phenomenon that makes it more difficult to see a star during the day (the background brightness of the sunlit sky masks the dimmer star) than at night (the star is brighter than the dark sky). Of course, if the fill-in light is too bright or lasts too long, it may cause a perceivable flash that is more distracting or annoying than the flicker caused by the relative movement of the exit pupil 12. Therefore, one can empirically determine the brightness and duration of the fill-in light that give the best result for a particular application. For example, the RSD system can generate a fill-in light that is as bright or approximately as bright as the average brightness of the image viewed through the exit pupil 12, that is the same or approximately the same average color as the image, or that is both the same brightness and color as the image. Furthermore, one can empirically determine the size and location of the illuminated FOV portion that gives the best results. For example, the RSD system can illuminate the viewer's entire composite FOV with the fill-in light. Or, the RSD system can illuminate a portion of the composite FOV, and this portion may or may not contain the exit pupil 12 at the time of the illumination.

FIG. 2 is a block diagram of a RSD system 40 that can generate a fill-in light to eliminate visual artifacts according to an embodiment of the invention, where like numbers are used to reference like elements with respect to FIG. 1. The system 40 includes a control circuit 42 and a movable optical assembly 44, which includes an image generator 46, fill-in light source 48, eye-position mechanism 50, image sensor 52, partially transmissive mirror 54, and mirrors 56 and 58. The image generator 46 generates one exit pupil 12, and the image viewed therethrough, for each of the viewer's eyes (only one eye 10 shown). The light source 48 generates the fill-in light within a flash field 59, and the mechanism 50 determines the viewing direction of the eye 10 with respect to the exit pupil 12 and, under the control of the circuit 42, tracks the exit pupil to shifts in the viewing direction. The sensor 52 measures the brightness, color, or both the brightness and color, of the exit-pupil image, and the control circuit 42 communicates with and controls the generator 46, light source 48, position mechanism 50, and sensor 52. In one embodiment, the image generator 46 is a mico-electro-mechanical (MEM) image scanner, examples of which are disclosed in commonly assigned U.S. Pat. No 6,245,590, issued Jun. 12, 2001, entitled "FREQUENCY TUNABLE RESONANT SCANNER AND METHOD OF MAKING," and U.S. application Ser. No. 09/816,809, filed Mar. 24, 2001, which is a continuation of U.S. Pat. No. 6,245,590, which are incorporated by reference. Likewise, an example of the eye-position mechanism 50 is disclosed in commonly assigned U.S. patent application Ser. No. 09/128,954, entitled "PERSONAL DISPLAY WITH VISION TRACKING", filed Aug. 5, 1998, which is incorporated by reference.

The operation of the RSD system 40 is now discussed in conjunction with FIGS. 1 and 2.

FIG. 2 depicts the relative positions of the assembly 44 and the eye 10 at time T1 when the center axis $24_{T1}$ of the eye's FOV $\mathbf{20}_{T1}$ (FIG. 1) is aligned with the exit pupil 12.

At time T2, the eye 10 begins rotating, thus causing the pupil 14 and the center axis 24 to rotate away from the exit pupil 12 and toward the path 30.

Also at time T2 or shortly thereafter, the eye-position mechanism 50 detects the rotation of the eye 10. In one embodiment, the image generator 46 directs an infrared tracking beam 60 onto the eye 10, which reflects the beam back to the eye-position mechanism 50 via the partially transmissive mirror 54 and the mirror 58. The eye's cornea 62 has a central region 64 that is aligned with the pupil 14. Because the central region 64 has a different reflectivity than the other regions of the cornea 62 and the eye's white part 66, the mechanism 50 can detect when the beam 60 is being reflected from a region of the eye 10 other than the central corneal region 64. In response to such detection, the control circuit 42 causes the mechanism 50 to move the assembly 44 so that beam 60 tracks the central corneal region 64, and, consequently, so that the exit pupil 12 tracks the center axis 24 of the FOV 20. This tracking operation is further discussed in U.S. patent application Ser. No. 09/128,954, entitled "PERSONAL DISPLAY WITH VISION TRACKING", which is incorporated by reference. But as stated above in conjunction with FIG. 1, because the mechanism 50 is often too slow to move the assembly 44 at the speed at which the eye 10 rotates, the exit pupil 12, and thus the image, may lag behind the center axis 24 for a period of time.

As discussed above in conjunction with FIG. 1, at time T3 the eye 10 stops rotating, and, at time T4, the exit pupil 12 "catches up" to the eye at the path 30.

Sometime between times T2 and T4, to reduce or eliminate potential flicker and/or other visual artifacts, the control circuit 42 activates the light source 48 in response to the mechanism 50 sensing misalignment of the eye 10 with the exit pupil 12. In some embodiments, some or all of the duration, brightness, and color of the fill-in light and the direction and aperture (not shown) of the light source 48 are preprogrammed into the control circuit 42—the aperture is the opening that determines the spread angle 68, and thus the size, of the flash field 59. In other embodiments, however, the control circuit 42 calculates one or more of these quantities based on the brightness and/or color of the exit-pupil image and on the length of the arc through which the eye 10 has rotated. For example, the image sensor 52 can sense the exit-pupil image via the partially transmissive mirror 58 and the mirror 56, and can determine the average brightness, average color, or both the average brightness and color of the exit-pupil image. The sensor 52 or control circuit 42 can add a scaling factor to account for the fact that the mirrors 56 and 58 direct only a portion of the image energy to the sensor 52. Alternatively, the control circuit 42 can determine the average brightness and/or average color from the electronic or optical signals (not shown) that the image generator 46 uses to generate the exit-pupil image. The control circuit 42 can then activate the light source 48 to generate the fill-in light having the same or approximately same average brightness, color, or both brightness and color as the exit-pupil image 12. Furthermore, the eye-position mechanism 50 can determine the relative position of the pupil 14 with respect to the exit pupil 12, and the control circuit 42 can set the aperture and/or direction of the light source 48 such that the fill-in light illuminates the desired portion of the eye's composite FOV.

Still referring to FIG. 2, in one embodiment the RSD system 40 includes two assemblies 44, one for each of the viewer's eyes. In this embodiment, each image generator 46 generates a respective exit pupil 12, and the image viewed therethrough, for a corresponding eye, each sensor 52 senses the brightness and/or color of the respective exit-pupil image, each mechanism 50 senses movement in the corresponding eye, and each light source 48 generates the fill-in light within a corresponding flash field 59. The system 40 may include two control circuits 42, one for each assembly 44, but preferably includes one common control circuit for both assemblies 44.

In another embodiment, the RSD system 40 includes single assembly 44 for both of the viewer's eyes. In this embodiment, the image generator 46 generates two exit pupils 12, one for each eye. For example, the assembly 44 may include optics, similar to the optics in a periscope or stereo microscope, that split a source image from the generator 46 into two exit-pupil images. The sensor 52 senses the brightness and/or color of the source image (either before or after the split), or the control circuit 42 determines the color and brightness of the source image from the signals (not shown) used to generate the source image. The mechanism 50 senses movement of the viewer's eyes. Because a viewer's eyes typically move in tandem, particularly when viewing a far-field object, the mechanism 50 may track the movement of only one eye. The light source 48 generates the fill-in light within at least a portion of the viewer's composite FOV.

Figure 3:
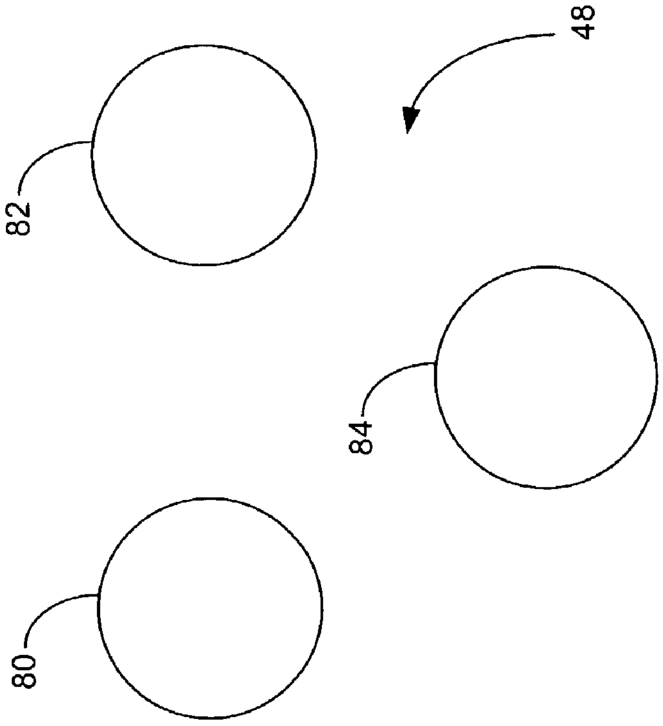
FIG. 3 is a diagram of the fill-in light source of FIG. 2 according to an embodiment of the invention.

FIG. 3 is a diagram of the fill-in light source 48 of FIG. 2 according to an embodiment of the invention. The source 48 includes three light-emitting diodes (LEDs) 80, 82, and 84 of different colors. For example, the LEDs 80, 82, and 84 may be red, green, and blue LEDs, respectively. By varying the intensities of the LEDs, the control circuit 42 (FIG. 2) can cause the source 48 to generate the fill-in light having virtually any desired color, brightness, or both color and brightness, such as the average color and brightness of the exit-pupil image as discussed above in conjunction with FIGS. 1 and 2. Alternatively, one can omit or deactivate two of the LEDs 80, 82, and 84 to convert the source 48 into a monochrome (single-color) light source. For example, one can omit the LEDs 82 and 84 and use a white LED 80. In this alternate embodiment, however, the light source 48 may be unable to match the color of the exit-pupil image. Or, one can omit or deactivate one of the LEDs 80, 82, and 84 to reduce the number of colors that the light source 48 can generate.

Referring to FIGS. 2 and 3, in one embodiment, the intensities of the LEDs 80, 82, and 84 are determined in the following manner.

First, a circuit—such as the control circuit 42 or the image generator 46—respectively sums the red, green, and blue components of the pixels of an image before the image is displayed via the exit pupil 12. For example, where the image is stored in a buffer—the buffer may be part of the control circuit 42 or the image generator 46—three adders (not shown), one for each color, can respectively sum the red, green, and blue pixel values for the image.

Next, the sums of the red, green, and blue pixel values are provided to the respective inputs of three digital-to-analog (D/A) converters—the D/A converters can be part of the control circuit 42 or the fill-in light source 48—that respectively generate red, green, and blue driving signals for the LEDs 80, 82, and 84.

When the eye-position mechanism 50 detects that the eye 10 has become misaligned with the exit pupil 12 as discussed above in conjunction with FIG. 2, the controller circuit 42 causes the D/A converters to drive the LEDs 80, 82, and 84 with the red, green, and blue driving signals, respectively. For example, the D/A converters may drive the LEDs via separate current drivers (not shown).

When the eye-position mechanism 50 detects that the eye 10 is or is almost realigned with the exit pupil 12, then the controller circuit 42 deactivates the LEDs 80, 82, and 84. The controller circuit 42 may deactivate the LEDs abruptly, or may decrease their intensities gradually to reduce the visual impact of an abrupt deactivation.

Alternatively, the summing circuit may sum only the red, green, and blue values for some but not all of the pixels in the image depending on the image-display rate, the image resolution, and other display parameters. Or the summing circuit may sum one or two color values for all the pixels, and the remaining color value(s) for only some of the pixels.

Figure 4:
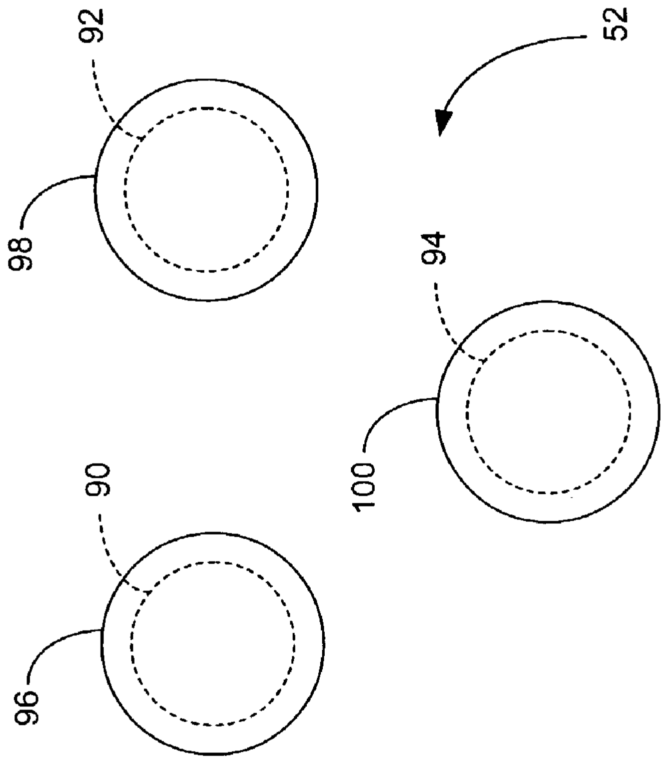
FIG. 4 is a diagram of the image sensor of FIG. 2 according to an embodiment of the invention.

FIG. 4 is a diagram of the image sensor 52 of FIG. 2 according to an embodiment of the invention. The sensor 52 includes three photo diodes 90, 92, and 94, which are respectively covered with color filters 96, 98, and 100. For example, the filters 96, 98, and 100 may be red, green, and blue filters, respectively. That is, the red filter allows only red light to pass through, the green filter passes only green light, and the blue filter passes only blue light. By reading the magnitudes of the currents generated by these photo diodes, the control circuit 42 (FIG. 2) can determine the brightness and color of the exit-pupil image. Alternatively, one can omit or deactivate two of the photo diodes 90, 92, and 94 to convert the sensor 52 into a monochrome (single-color) sensor. In this alternate embodiment, however, the sensor 52 may be unable to sense the color of the exit-pupil image. Or, one can omit or deactivate one of the photo diodes 90, 92, and 94 to reduce the number of colors that the sensor 52 can distinguish.

Figure 5:
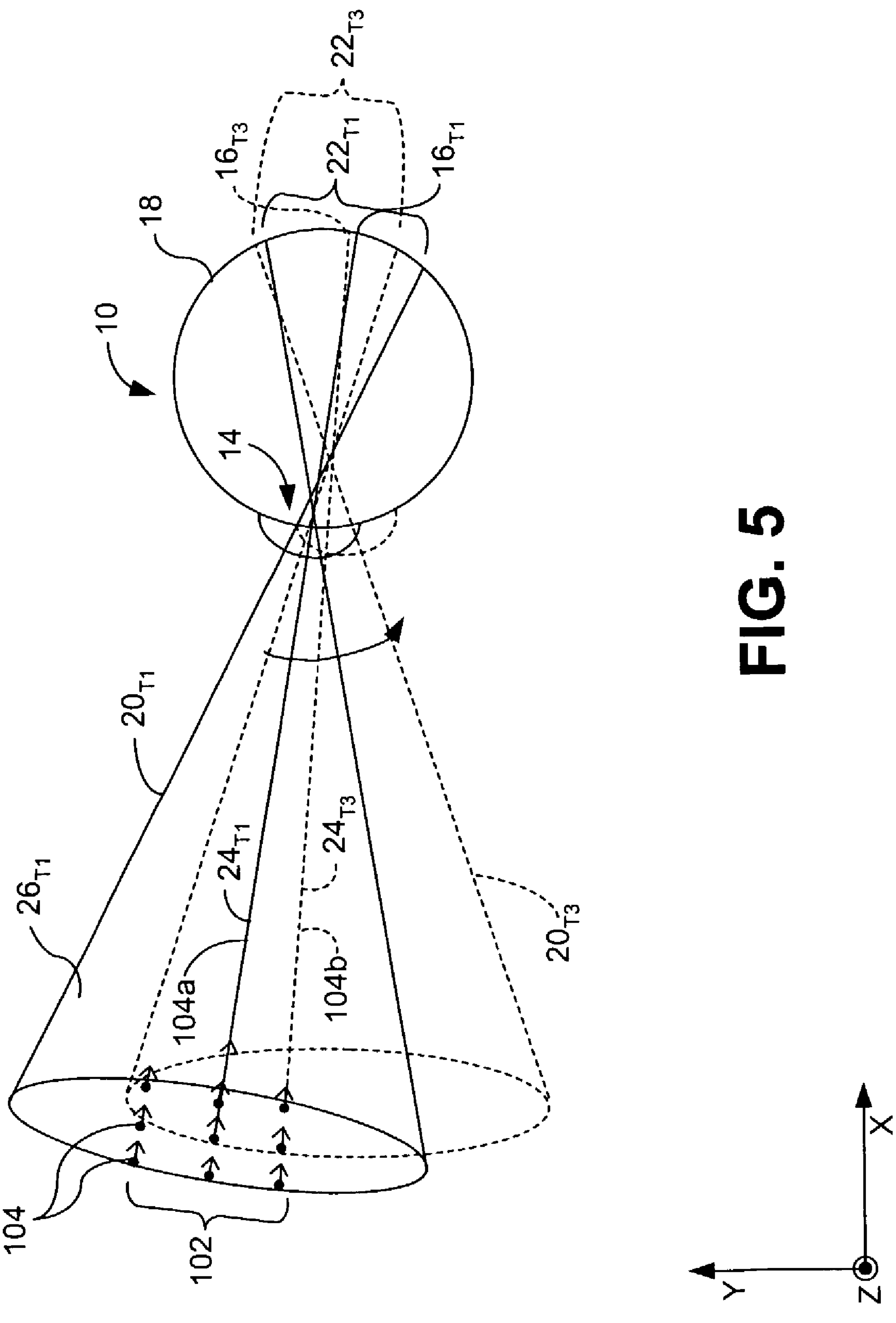
FIG. 5 is a diagram that shows how a display system such as an expanded-exit-pupil RSD system can reduce or eliminate visual artifacts such as flicker as a viewer shifts his gaze according to an embodiment of the invention.

FIG. 5 is a diagram that shows how a RSD system (not shown in FIG. 5) can reduce or eliminate visual artifacts as a viewer shifts his gaze according to another embodiment of the invention where the system generates an expanded exit pupil 102 having multiple—here nine—exit pupils 104, each of which allows the viewer to perceive identical or approximately identical exit-pupil images. For purposes of explanation, the page that FIG. 5 is drawn on lies in the X-Y plane, the Z axis is perpendicular to the page, and like elements have like reference numbers with respect to FIG. 1. Furthermore, although only one eye is shown and discussed, a similar discussion applies to the viewer's other eye (not shown).

At time T1, the viewer's eye 10 is in a steady-state position and is gazing straight ahead such that the center axis $\mathbf{24}_{T1}$ of the viewer's FOV $\mathbf{20}_{T1}$ is aligned with the exit pupil 104*a* and the lens (not shown) of the eye focuses the corresponding exit-pupil image onto the center region $\mathbf{16}_{T1}$ of the retina 18.

At time T2, the eye 10 begins rotating toward an exit pupil 104*b*, and the eye's pupil 14 and FOV 20 follow the rotation of the eye.

At time T3, the eye 10 stops rotating and enters into a steady-state position where the FOV center axis $\mathbf{24}_{T3}$ is aligned with the exit pupil 104*b* and intersects the center region $\mathbf{16}_{T3}$ of the retina 18.

At time T2 or shortly thereafter, the RSD system (not shown in FIG. 5) detects that the eye 10 is rotating away from the exit pupil 104*a*. The distance between the exit pupil 104*a* and the FOV center axis 24 increases such that the exit pupil, and thus the image viewed therethrough, effectively moves from the eye's straight-ahead zone of vision to its peripheral zone of vision (or altogether out of the eye's zone of vision).

At a time T4 after the eye 10 stops rotating—the eye stops rotating at time T3—the FOV center axis $\mathbf{24}_{T3}$ is aligned with the exit pupil 104*b*.

As discussed in the Background section of this application, the viewer (not shown) may perceive flicker or other visual artifacts during the period between times T2 and T4 when the exit pupil 104*a*, and thus the image, effectively moves from the viewer's straight-ahead zone of vision to (and maybe beyond) his peripheral zone of vision, and the exit pupil 104*b*, and thus the image, effectively moves from the viewer's peripheral zone of vision (or beyond) to his straight-ahead zone of vision.

Furthermore, the viewer's other eye (not shown) shifts its alignment from one exit pupil to another (not shown) in the same way as the eye 10 shifts its alignment from the exit pupil 104*a* to the exit pupil 104*b* during the period between T2-T4.

Still referring to FIG. 5, in one embodiment, the RSD system (not shown in FIG. 5) reduces or eliminates the viewer's (viewer not shown) perception of visual artifacts during the period between times T2 and T4 by briefly illuminating at least a portion of the viewer's composite FOV. This fill-in light makes the eye's shift from the exit pupil 104*a* to the exit pupil 104*b* less noticeable by temporarily raising the brightness level of the illuminated portion of the viewer's composite FOV. As discussed above in conjunction with FIGS. 1 and 2, one can empirically determine the duration, brightness, color, spread, and direction of the fill-in light that give the best result for a particular application. For example, the RSD system (not shown in FIG. 5) can generate a fill-in light that is as bright or as approximately as bright as the average brightness of the exit-pupil image, that is the same or approximately the same average color as the exit-pupil image, or that is both the same brightness and color as the exit-pupil image. The exit-pupil image on which the brightness and/or color of the fill-in light is based may be the one viewed through the exit pupil 104*a*, the one viewed through the exit pupil 104*b*, or a combination of both. Furthermore, the RSD system can illuminate the viewer's entire composite FOV or a portion of the FOV 20 for one or both eyes.

Still referring to FIG. 5, one can modify the RSD system 40 of FIG. 2 to function as described above. In one embodiment, because the system 40 need not track the exit pupils 104 to movements of the eye 10, one can remove or deactivate the portion of the eye-position mechanism 50 that moves the assembly 44. Furthermore, one can modify the image generator 46 to generate the expanded exit pupil 102 having nine or another number of exit pupils 104. A technique for generating an expanded exit pupil such as the expanded exit pupil 102 is disclosed in commonly assigned U.S. patent application Ser. No. 10/205,858, filed Jul. 26, 2002, entitled APPARATUS AND METHODS FOR GENERATING MULTIPLE EXIT-PUPIL IMAGES IN AN EXPANDED EXIT PUPIL, and commonly assigned U.S. patent application Ser. No. 10/206,177, filed Jul. 26, 2002, entitled APPARATUS AND METHODS FOR GENERATING MULTIPLE EXIT-PUPIL IMAGES IN AN EXPANDED EXIT PUPIL, which are incorporated by reference.

Moreover, in some instances, the pupil 14 may not be perfectly aligned with one of the exit pupils 104 at steady-state times T1 and T3. But the exit pupils 104 are typically packed densely enough so that the viewer (not shown) can focus on at least one of the exit pupils 104 regardless of the direction in which he is gazing.

Figure 6:
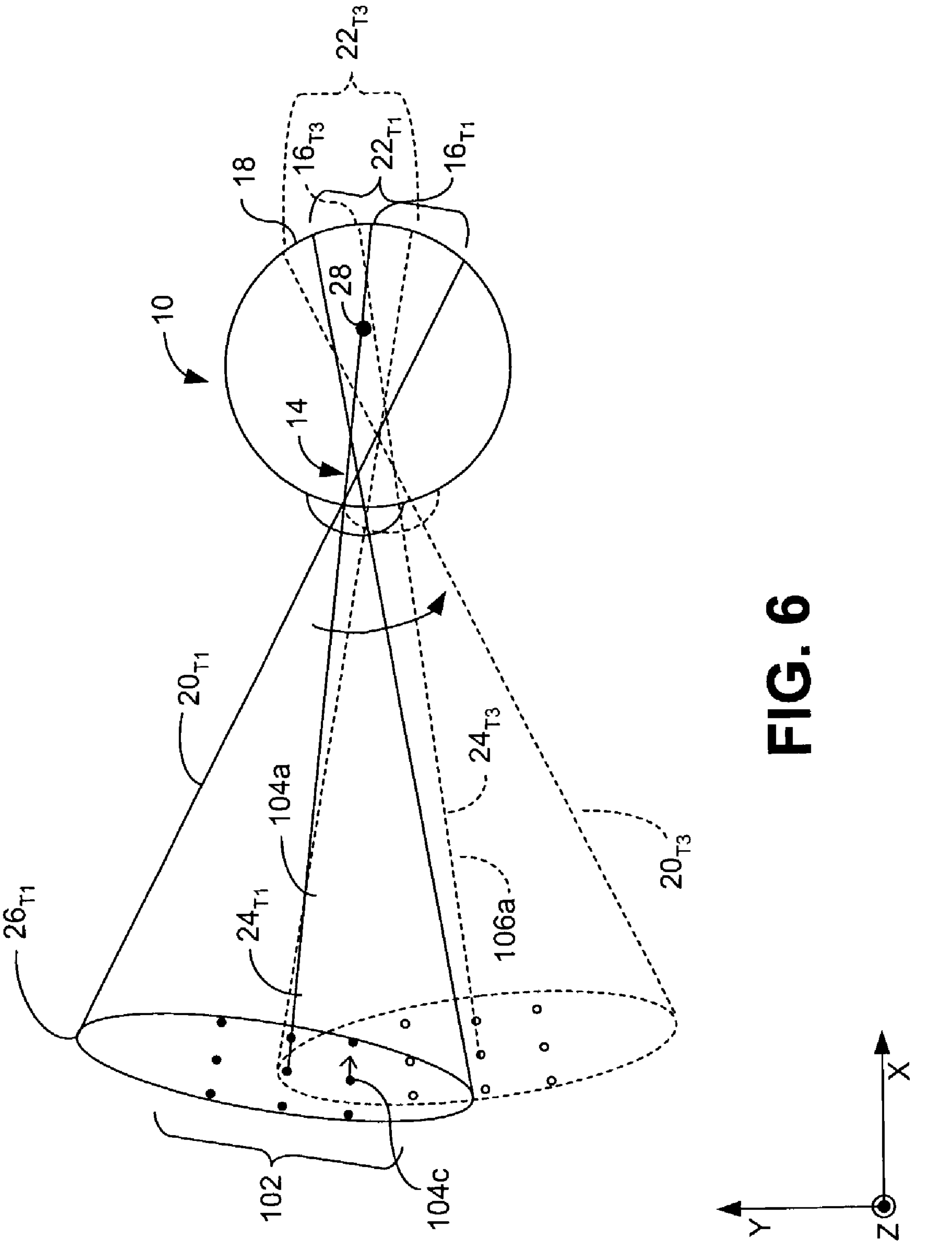
FIG. 6 is a diagram that shows how a display system such as a combination tracking and expanded-exit-pupil RSD system can reduce or eliminate visual artifacts such as flicker as a viewer shifts his gaze according to an embodiment of the invention.

FIG. 6 is a diagram that shows how a RSD system (not shown in FIG. 5) can reduce or eliminate visual artifacts as a viewer shifts his gaze according to another embodiment of the invention where the system generates an expanded exit pupil 102 and tracks the expanded exit pupil to movements of the eye 10. For purposes of explanation, the page that FIG. 6 is drawn on lies in the X-Y plane, the Z axis is perpendicular to the page, and like elements have like reference numbers with respect to FIGS. 1 and 5. Furthermore, although only one eye is shown and discussed, a similar discussion applies to the viewer's other eye (not shown).

At time T1, the viewer's eye 10 is in a steady-state position and is gazing straight ahead such that the center axis $\mathbf{24}_{T1}$ of the FOV $\mathbf{20}_{T1}$ is aligned with the exit pupil 104*a* such that lens (not shown) of the eye 10 focuses the exit-pupil image onto the center region $\mathbf{16}_{T1}$ of the retina 18.

At time T2, the eye 10 begins rotating toward a path 106*a*, and the eye's pupil 14 and FOV 20 follow the rotation of the eye.

At time T3, the eye 10 stops rotating and enters into a steady-state position where the center axis $\mathbf{24}_{T3}$ of the FOV $\mathbf{20}_{T3}$ is aligned with the path 106*a*, which, like the FOV center axis $\mathbf{24}_{T3}$, intersects the center region $\mathbf{16}_{T3}$ of the retina 18.

At time T2 or shortly thereafter, the eye-position mechanism (such as the mechanism 50 of FIG. 2) detects that the eye 10 is rotating away from the exit pupil 104*a*, and attempts to track this rotation by keeping the exit pupil 104*a* aligned with the FOV center axis 24. But if the eye 10 rotates too fast, then the eye-position mechanism can't keep up, and the exit pupil 104*a* lags behind the center axis 24. Initially, the distance between the exit pupil 104*a* and center axis 24 increases such that the exit pupil 104*a*, and thus the image it defines, effectively move from the eye's straight-ahead zone of vision to its peripheral zone of vision (or altogether outside of the eye's zone of vision). In addition, the exit pupil 104*c* may effectively move into and out of the viewer's straight-ahead and/or peripheral zone of vision depending on how fast the viewer shifts his gaze and how close the exit pupils 104*a* and 104*c* are to one another.

At time T4 after the eye 10 stops rotating, the exit pupil 104*a* "catches up" to the center axis $\mathbf{24}_{T3}$ by moving into alignment with the path 106*a*, and thus by moving back into the eye's straight-ahead zone of vision.

As discussed in the Background section of this application, the viewer (not shown) may perceive flicker or other visual artifacts during the period between times T2 and T4 when the exit pupil 104*a* (and possibly the exit pupil 104*c*) effectively moves from the eye's straight-ahead zone of vision, to (and maybe beyond) its peripheral zone of vision, and back into its straight-ahead zone of vision.

Furthermore, the viewer's other eye (not shown) and the exit pupil(s) (not shown) viewed by that eye act the same way as the eye 10 does with respect to the exit pupil 104*a* (and possibly the exit pupil 104*c*) during the period from T1-T4.

Still referring to FIG. 6, in one embodiment, the RSD system (not shown in FIG. 6) reduces or eliminates the viewer's (viewer not shown) perception of visual artifacts during the period between times T2 and T4 by illuminating at least a portion of the viewer's composite FOV. This fill-in light makes the eye's shift from the exit pupil 104*a* to the path 106*a* less noticeable by temporarily raising the brightness level of the illuminated portion of the viewer's composite FOV. As discussed above in FIGS. 1 and 5, one can empirically determine the duration, brightness, color, spread, and direction of the fill-in light that give the best results for a particular application.

Still referring to FIG. 6, one can modify the RSD system 40 of FIG. 2 to function as described above. For example, one can modify the image generator 46 to generate the expanded exit pupil 102 as discussed above in conjunction with FIG. 5.

The foregoing discussion is presented to enable a person skilled in the art to make and use the invention. Various modifications to the embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein.

What is claimed:

1. A display system, comprising:

an image generator operable to generate an image; and a control circuit coupled to the image generator and operable to reduce or eliminate a viewer's perception of a visual artifact when the viewer's gaze shifts with respect to the image by generating a visible fill-in light.

2. The display system of claim 1 wherein the control circuit is operable to reduce or eliminate the viewer's perception of flicker when the viewer's gaze shifts with respect to the image.

3. The display system of claim 1 wherein the control circuit is operable to generate the fill-in light in response to the viewer's gaze shiftings with respect to the image.

4. The display system of claim 1 wherein:

the image has a brightness level; and the control circuit is operable to generate the fill-in light having the same or approximately the same brightness level as the image.

5. The display system of claim 1 wherein:

the image has a color; and the control circuit is operable to generate the fill-in light having the same or approximately the same color as the image.

6. The display system of claim 1 wherein:

the image has a brightness level and a color; and the control circuit is operable to generate the fill-in light having the same or approximately the same brightness level and color as the image.

7. The display system of claim 1 wherein the image generator is operable to generate the image within an exit pupil.

8. A display system, comprising:

an image generator operable to generate an image;

a position circuit operable to determine a direction of a viewer's gaze, the viewer having a field of view;

a light source operable to brighten a portion of the viewer's field of view with visible light; and a control circuit coupled to the image generator, position circuit, and light source, and operable to align the image with the viewer's gaze and to activate the light source before or while aligning the image.

9. The display system of claim 8 wherein the image generator is operable to:

modulate a light beam; and scan the light beam to generate the image.

10. The display system of claim 8 wherein the position circuit is operable to determine the direction of the viewer's gaze with respect to the image.

11. The display system of claim 8 wherein the light source comprises a light-emitting diode.

12. The display system of claim 8 wherein the control circuit is operable to:

detect when the image and the viewer's gaze become misaligned;

realign the image with the viewer's gaze; and activate the light source after detecting that the image and viewer's gaze have become misaligned but before the image is realigned with viewer's gaze.

13. The display system of claim 8 wherein the light source is operable to brighten the viewer's entire field of view.

14. A display system, comprising:

an image generator operable to generate an image having an image brightness level;

a position circuit operable to determine a position of a viewer's pupil, the viewer having a field of view;

a light source operable to illuminate a portion of the viewer's field of view with an illumination brightness level of visible light; and a control circuit coupled to the image generator, position circuit, and light source, and operable to align the image with the pupil, to set the illumination brightness level equal or approximately equal to the image brightness level, and to activate the light source before or while aligning the image with the pupil.

15. The display system of claim 14 wherein:

the image generator is operable to generate the image from an image signal; and the control circuit is operable to determine the image brightness level from the image signal.

16. The display system of claim 14 wherein the light source emits white light.

17. The display system of claim 14, further comprising a sensor coupled to the control circuit and operable to determine the image brightness level.

18. The display of claim 14 wherein:

the image has an average brightness level; and the control circuit is operable to set the illumination brightness level equal or approximately equal to the average brightness level of the image.

19. The display system of claim 14 wherein the light source is operable to brighten the entire portion of the viewer's field of view attributable to the viewer's pupil.

20. A display system, comprising:

an image generator operable to generate an image having an image color;

a position circuit operable to determine a position of a viewer's pupil, the viewer having a field of view;

a light source operable to illuminate a portion of the viewer's field of view with an illumination color of visible light; and a control circuit coupled to the image generator, position circuit, and light source, and operable to align the image with the pupil, to set the illumination color equal or approximately equal to the image color, and to activate the light source before or while aligning the image with the pupil.

21. The display system of claim 20 wherein:

the image generator is operable to generate the image from an image signal; and the control circuit is operable to determine the image color from the image signal.

22. The display system of claim 20 wherein the light source comprises first, second, and third light-emitting diodes respectively having first, second, and third colors.

23. The display system of claim 20, further comprising a sensor coupled to the control circuit and operable to determine the image color.

24. The display of claim 20 wherein:

the image has an average color; and the control circuit is operable to set the illumination color equal or approximately equal to the average color of the image.

25. A method, comprising:

generating an exit pupil via which a viewer receives an image; and reducing or eliminating a visual artifact when the viewer's gaze shifts with respect to the exit pupil by generating a visible fill-in light.

26. The method of claim 25 wherein reducing or eliminating a visual artifact comprises reducing or eliminating flicker when the viewer's gaze shifts with respect to the exit pupil.

27. The method of claim 25 wherein reducing or eliminating a visual artifact comprises generating the fill-in light in response to the viewer's gaze shifting with respect to the exit pupil.

28. The method of claim 25 wherein reducing or eliminating a visual artifact comprises generating the fill-in light having the same or approximately the same brightness level as the image.

29. The method of claim 25 wherein reducing or eliminating a visual artifact comprises generating the fill-in light having the same or approximately the same color as the image.

30. The method of claim 25 wherein reducing or eliminating a visual artifact comprises generating the fill-in light having the same or approximately the same brightness level and color as the image.

31. The method of claim 25, further comprising generating the exit pupil by scanning an intensity-modulated light beam.

32. A method, comprising:

aligning an image exit pupil with a viewer's gaze; and temporarily and visibly brightening a portion of the viewer's field of view before the exit pupil is aligned with the viewer's gaze.

33. The method of claim 32 wherein:

aligning the exit pupil comprises detecting when the exit pupil and viewer's gaze become misaligned and realigning the exit pupil with the viewer's gaze; and temporarily brightening the portion of the field of view comprises temporarily brightening the portion after detecting the misalignment but before the exit pupil is realigned with the viewer's gaze.

34. The method of claim 32 wherein temporarily brightening the portion of the field of view comprises temporarily brightening the portion to reduce or eliminate the viewer's perception of flicker.

35. A method, comprising:

aligning an image with a viewer's pupil, the image having a brightness level; and before the image is aligned with the pupil, illuminating a portion of the viewer's field of view with visible light having a level of brightness that is or is approximately equal to the brightness level of the image.

36. The method of claim 35, further comprising:

generating the image from an image signal; and determining the brightness level of the image from the image signal.

37. The method of claim 35, further comprising measuring the brightness level of the image.

38. The method of claim 35 wherein illuminating a portion of the field of view comprises illuminating the portion with visible light having a level of brightness that is or is approximately equal to the average brightness level of the image.

39. A method, comprising:

aligning an image with a viewer's pupil, the image having a color; and before the image is aligned with the pupil, illuminating a portion of the viewer's field of view with visible light having a color that is or is approximately equal to the color of the image.

40. The method of claim 39, further comprising:

generating the image from an image signal; and determining the color of the image from the image signal.

41. The method of claim 39 wherein illuminating the portion of the viewer's field of view comprises illuminating the portion with visible light from light-emitting diodes each having a different color.

42. The method of claim 39, further comprising measuring the color of the image.

43. The method of claim 39 wherein illuminating a portion of the viewer's field of view comprises illuminating the portion with visible light having a color that is or is approximately equal to the average color of the image.

44. The display system of claim 1 wherein the control circuit is operable to generate the fill-in light for a predetermined duration.

45. The method of claim 25 wherein reducing or eliminating a visual artifact comprises generating the fill-in light for a predetermined length of time.

* * * * *